United States Patent
Sakaida

(10) Patent No.: US 6,724,857 B2
(45) Date of Patent: Apr. 20, 2004

(54) METHOD, APPARATUS AND PROGRAM FOR RADIATION IMAGING

(75) Inventor: Hideyuki Sakaida, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/426,852

(22) Filed: May 1, 2003

(65) Prior Publication Data

US 2003/0215061 A1 Nov. 20, 2003

(30) Foreign Application Priority Data

May 16, 2002 (JP) .................................... 2002-141000

(51) Int. Cl.$^7$ ............................................. G01N 23/04
(52) U.S. Cl. .......................................... 378/62; 378/98
(58) Field of Search ................................ 378/4, 62, 98, 378/98.9

(56) References Cited

U.S. PATENT DOCUMENTS 3,771,116 A * 11/1973 Farrah ............................ 367/8
6,397,099 B1 * 5/2002 Chance ........................ 600/473
6,493,422 B2 * 12/2002 Wilkins et al. .............. 378/98.9

OTHER PUBLICATIONS

T.E. Gureyev et al., Quantitative In–Line Phase–Contrast Imaging With Multienergy X Rays, Physical Review Letters, vol. 86, No. 25., Jun. 18, 2001, The American Physical Society.

* cited by examiner

Primary Examiner—David V. Bruce
(74) Attorney, Agent, or Firm—Sughrue Mion, PLLC

(57) ABSTRACT

To provide a radiation imaging method using a phase contrast method capable of imaging efficiently with high estimation accuracy of restoring phase. The radiation imaging method includes, the steps of: (a) sequentially detecting intensity of radiation transmitted through an object at plural distances from the object in first order by using radiation having a first wavelength to obtain a first group of image signals; (b) sequentially detecting intensity of radiation transmitted through the object at plural distances from the object in the reverse order by using radiation having a second wavelength to obtain a second group of image signals; (c) restoring phase information of the radiation based on the first and second groups of image signals to obtain plural pieces of phase data; and (d) generating image data based on the plural pieces of phase data.

3 Claims, 8 Drawing Sheets

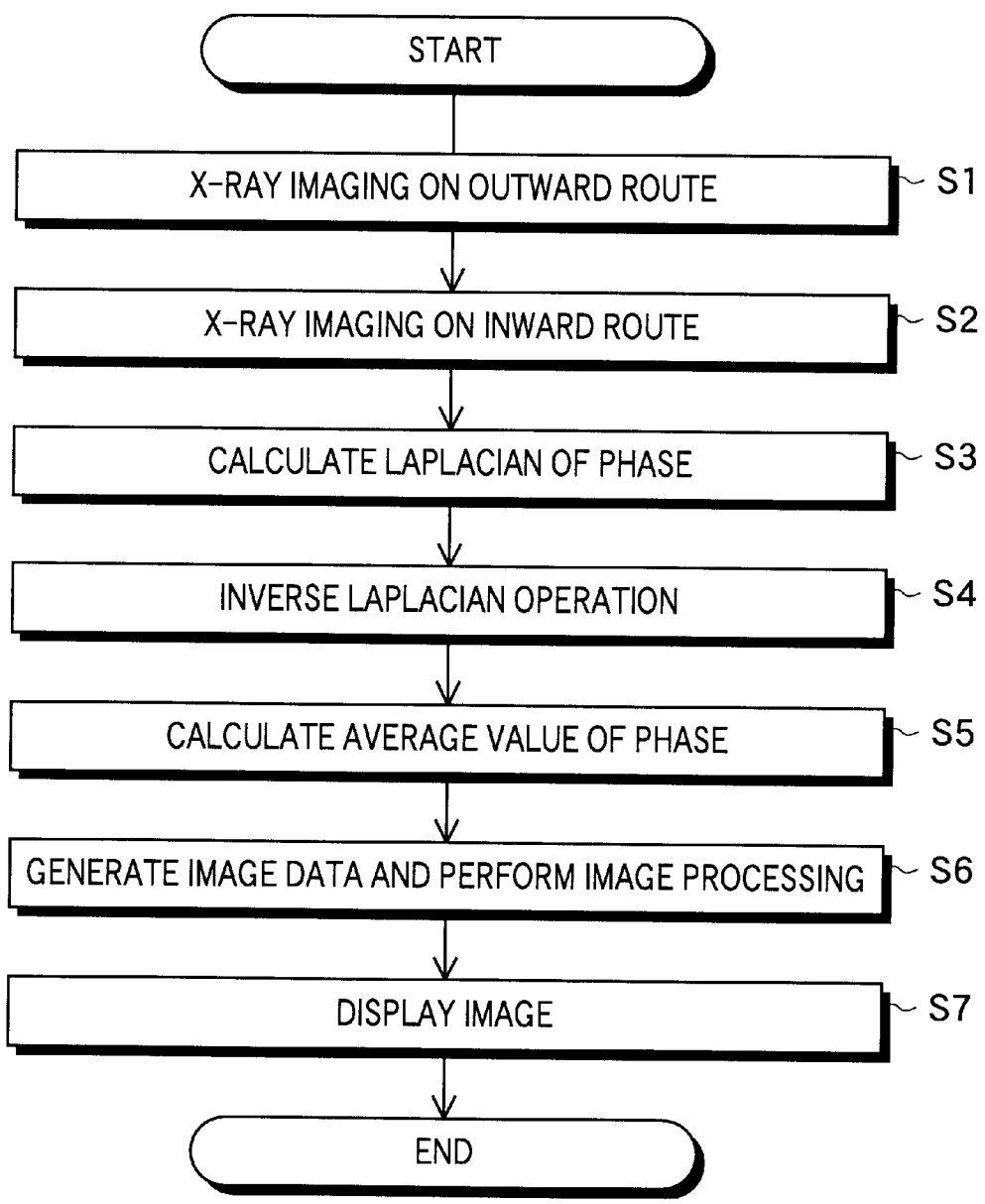

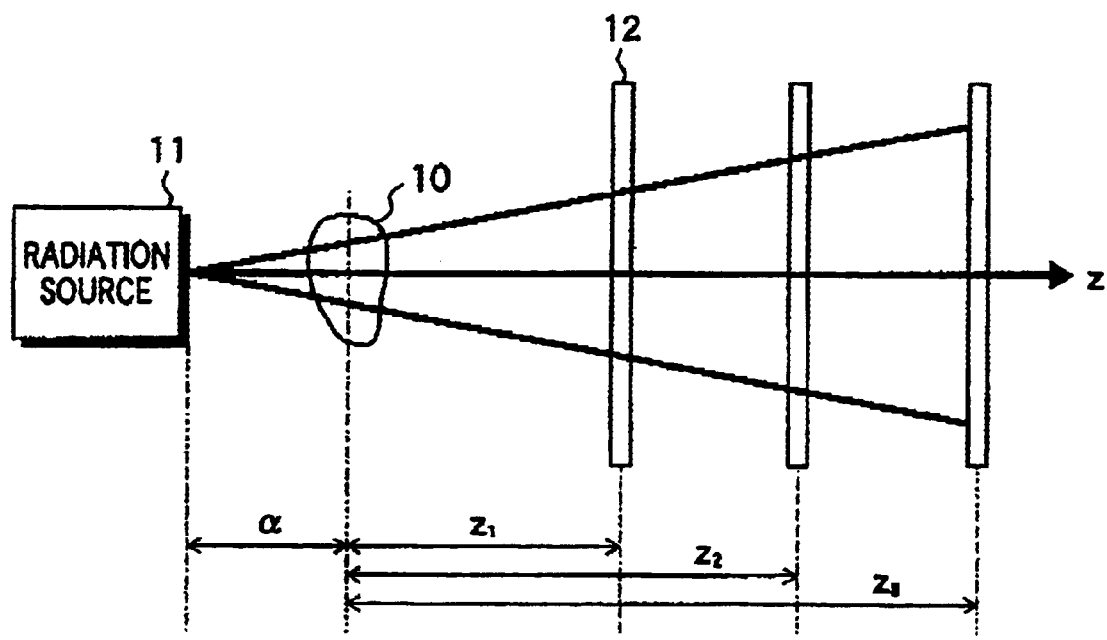

METHOD, APPARATUS AND PROGRAM FOR RADIATION IMAGING

BACKGROUND OF THE INVENTION

1. Field of the Invention

The present invention relates to a method, an apparatus and a program for radiation imaging, which are used for constituting an image on the basis of radiation image information obtained by radiation imaging. In this application, the word "radiation" is used in a wide sense so as to include a corpuscular beam such as an electron beam, or an electromagnetic wave, in addition to a general radiation such as X-rays, α-rays, β-rays, γ-rays, ultraviolet rays and the like.

2. Description of a Related Art

Conventionally, an imaging method using X-rays or the like is utilized in various fields, and employed as one of the most important means for diagnosis, particularly, in a medical field. Since a first X-ray photograph was realized, X-ray photography has been repeatedly improved and a method using a combination of a fluorescent screen and an X-ray film is predominantly used at present. On the other hand, in recent years, various digitized devices such as X-ray CT, ultrasonic or MRI are in practical use and establishment of a diagnostic information processing system and the like in hospitals is being promoted. As for X-ray images, many studies have also been made for digitizing an imaging system. The digitization of the imaging system not only enables a long-term preservation of a large amount of data without incurring deterioration in image quality but also contributes to development into the medical diagnostic information system.

Incidentally, a radiation image obtained as described above is generated by converting intensity of radiation transmitted through an object into brightness of the image. For example, in the case of imaging a region including a bone part, the radiation transmitted through the bone part is largely attenuated, and the radiation transmitted through a region other than the bone part, namely, a soft part is slightly attenuated. In this case, since the difference in the intensity of the radiation transmitted through different tissues is large, the radiation image with high contrast can be obtained.

On the other hand, for example, in the case of imaging a region of the soft part such as a breast, since the radiation is easily transmitted through the soft part as a whole, the difference between tissues in the soft part hardly appears as the difference in the intensity of the transmitted radiation. Because of this, as for the soft part, only a radiation image with low contrast can be obtained. Thus, the radiation imaging method is not suitable as a method of visualizing slight difference between tissues in the soft part.

Herein, information contained in radiation transmitted through an object includes phase information in addition to intensity information. In recent years, a phase contrast method has been studied in which an image is generated by using the phase information. The phase contrast method is an image construction technique for converting the phase difference resulted by transmitting X-rays or the like through the object into the brightness of the image.

Examples of the phase contrast method include a method of obtaining the phase difference on the basis of interference light generated by using an interferometer or a zone plate, and a method of obtaining the phase difference on the basis of diffracted light. Among them, in the method of obtaining the phase difference on the basis of the diffracted light, which method is called as a diffraction method, the phase difference is obtained on the basis of the following principle. For example, X-ray propagates through substance by travel of waves similar to light. Propagation velocity thereof varies depending on a refractive index of the substance. Therefore, when irradiating an object with an X-ray that has a uniform phase, the way the X-ray propagates varies in accordance with the difference between tissues in the object. For this reason, a wave front of the X-ray transmitted through the object is distorted and, as a result, diffraction fringes are produced on an X-ray image obtained on the basis of the transmitted X-ray. A pattern of the diffraction fringes varies depending on the distance between a screen on which the X-ray image is formed and the object, or wavelength of the X-ray. Accordingly, by analyzing two or more sheets of X-ray images having different diffraction fringe patterns, phase difference of X-rays, which is produced at each position of the screen, can be obtained. By converting the phase difference into the brightness, the X-ray image, in which difference between tissues in the object clearly appears, can be obtained.

In particular, in the radiation transmitted through a soft part of an object, the phase difference is larger than the intensity difference depending on the difference of tissues through which the radiation has transmitted. Therefore, delicate difference between tissues can be visualized by using the phase contrast method.

For the purpose of using such a phase contrast method, imaging conditions in performing the radiation imaging or techniques for restoring the phase from the diffraction fringe patterns are being studied. For example, T. E. Gureyev et al. "Quantitative In-Line Phase-Contrast Imaging with Multi-energy X Rays", PHYSICAL REVIEW LETTERS Vol. 86, No. 25 (2001), pp. 5827–5830 discloses that the phase restoration is performed on the basis of image information obtained by X-ray imaging with three types of X-rays having different wavelength respectively.

In the reference, relationship between phase and intensity of the X-ray just after having transmitted through an object to be inspected, and intensity of the X-ray at a predetermined distance from the object is noticed. That is, in the reference, as shown in FIG. 8, the X-ray imaging is performed on the assumption of such configuration that three types of X-rays having wavelength of $\lambda_0$, $\lambda_1$ and $\lambda_2$ respectively transmit through an object 100 to be inspected and enter a screen 102 disposed at a distance of R from an object plane 101.

In this case, relationship represented by the following expression stands up between intensity $I(r_\perp, 0, \lambda_0)$ and phase $\phi(r_\perp, 0, \lambda_0)$ of the X-ray just after having transmitted through the object 100 to be inspected, and intensity $I(r_\perp, R, \lambda_m)$ of the X-ray diffraction light detected on the screen 102, provided that in the following expression (1), $I(r_\perp, 0, \lambda 0) = \exp\{-M(r_\perp, 0, \lambda_0)\}$ $$A \begin{pmatrix} M(r_\perp, 0, \lambda_0) \\ -\nabla^2 \phi(r_\perp, 0, \lambda_0) \\ \nabla M \cdot \nabla \phi(r_\perp, 0, \lambda_0) \end{pmatrix} = \begin{pmatrix} g_0 \\ g_1 \\ g_2 \end{pmatrix} \quad (1)$$

where $$A = \begin{pmatrix} -1 & \gamma_0 & \gamma_0 \\ -\sigma_1^3 & \sigma_1\gamma_1 & \sigma_1^4\lambda_1 \\ -\sigma_2^3 & \sigma_2\gamma_2 & \sigma_2^4\gamma_1 \end{pmatrix}$$

provided that $$\sigma_m = \frac{\lambda_m}{\lambda_0}, \gamma_m = \frac{R\lambda_m}{2\pi},$$

$$g_m = ln\{I(r_\perp, R, \lambda_m)\} \; (m=0,1,2)$$

In the expression (1), when $\nabla M \cdot \nabla \phi(r_\perp, 0, \lambda_0)$ is sufficiently small, it can be approximated as follows.

$$\begin{pmatrix} -1 & \gamma_0 \\ -\sigma_1^3 & \sigma_1\gamma_1 \end{pmatrix} \begin{pmatrix} M(r_\perp, 0, \lambda_0) \\ -\nabla^2\phi(r_\perp, 0, \lambda_0) \end{pmatrix} = \begin{pmatrix} g_0 \\ g_1 \end{pmatrix} \quad (2)$$

Further, from the expression (2), the intensity and the phase of the X-ray just after having transmitted through the object 100 to be inspected are represented as follows.

$$M(r_\perp, 0, \lambda_0) = \frac{\lambda_0}{\Delta\lambda}(g_0 - \sigma^{-2}g_1) \quad (3)$$

$$-\nabla^2\phi(r_\perp, 0, \lambda_0) = \frac{2\pi}{R\Delta\lambda}(\sigma g_0 - \sigma^{-2}g_1) \quad (4)$$

By performing an inverse Laplace operation on Laplace $\nabla\phi^2(r_\perp, 0, \lambda_0)$ of phase in the expression (4), the phase $\phi(r_\perp, 0, \lambda_0)$ can be obtained. Further, by converting the phase into brightness of the image, a visible image representing the object can be obtained. By utilizing the expression (4) as just described, an operation for restoring phase can be simply performed on the basis of a small number of radiation images obtained while changing wavelength.

However, when phase is restored on the basis of about two or three radiation images, there arises a problem that, in the case where image quality is deteriorated due to influence of noise or the like, accuracy of the phase restoration deteriorates. In order to elevate the accuracy of phase restoration, it is considered to increase the number of radiation images by imaging while changing wavelength of the radiation applied to the object, however, when the wavelength is changed by using one radiation source, it takes a long time whenever the wavelength is changed. Further, when a plurality of radiation sources generating radiation different in wavelength are used, an apparatus becomes large size. On the other hand, it is also considered to increase the number of radiation images by imaging while changing not wavelength of radiation, but distance between the object plane 101 and the screen 102. However, there arises a problem that the apparatus becomes large size because moving distance of the screen 102 increases.

SUMMARY OF THE INVENTION

The present invention has been accomplished to solve the above-mentioned problems. A first object of the present invention is to provide a radiation imaging method capable of efficiently performing the imaging within a short period of time, as well as performing phase restoration with high estimation accuracy upon constituting a radiation image by using a phase contrast method. A second object of the present invention is to provide a radiation imaging apparatus for performing such a radiation imaging and a radiation imaging program for allowing a CPU to execute such a radiation imaging.

In order to solve the above-mentioned problems, a radiation imaging method according to the present invention comprises the steps of: (a) sequentially detecting, by using radiation having a first wavelength, intensity of radiation transmitted through an object on a plurality of planes different in distance from the object in a first order of increasing or decreasing the distance from the object so as to obtain a first group of image signals representing radiation image information on the plurality of planes respectively; (b) sequentially detecting, by using radiation having a second wavelength different from the first wavelength, intensity of radiation transmitted through the object on a plurality of planes different in distance from the object in a second order reverse to the first order so as to obtain a second group of image signals representing radiation image information on the plurality of planes respectively; (c) restoring phase information of the radiation transmitted through the object on the basis of the first group of image signals and the second group of image signals so as to obtain plural pieces of phase data; and (d) generating image data on the basis of the plural pieces of phase data obtained at step (c).

A radiation imaging apparatus according to the present invention comprises: a variable wavelength radiation source capable of generating radiation having a first wavelength and radiation having a second wavelength different from the first wavelength; detection means for detecting intensity of radiation transmitted through an object so as to obtain an image signal representing radiation image information; driving means to be used for altering distance between the object and the detection means; control means for controlling the variable wavelength radiation source and the driving means in such a manner that the detection means sequentially detects, by using radiation having a first wavelength, intensity on a plurality of planes different in distance from the object in a first order of increasing or decreasing the distance from the object, and then, the detection means sequentially detects, by using radiation having a second wavelength, intensity on a plurality of planes different in distance from the object in a second order reverse to the first order; and image constructing means for restoring phase information of the radiation transmitted through the object on the basis of a plurality of image signals obtained by disposing the detection means at a plurality of positions different in distance from the object so as to obtain plural pieces of phase data, and generating image data on the basis of the plural pieces of phase data.

A radiation imaging program according to the present invention actuates a CPU to execute the procedures of: (a) sequentially detecting, by using radiation having a first wavelength, intensity of radiation transmitted through an object on a plurality of planes different in distance from the object in a first order of increasing or decreasing the distance from the object so as to obtain a first group of image signals representing radiation image information on the plurality of planes respectively; (b) sequentially detecting, by using radiation having a second wavelength different from the first wavelength, intensity of radiation transmitted through the object on a plurality of planes different in distance from the object in a second order reverse to the first order so as to obtain a second group of image signals representing radiation image information on the plurality of planes respectively; (c) restoring phase information of the radiation transmitted through the object on the basis of the first group of image signals and the second group of image signals so as to obtain plural pieces of phase data; and (d) generating image data on the basis of the plural pieces of phase data obtained in the procedure (c).

In this application, the phrase "radiation having a first wavelength or a second wavelength" is used so as to include not only radiation having a single wavelength but also radiation which has radiation intensity distribution in a plurality of wavelengths containing the first wavelength or the second wavelength as the central wavelength and which is regarded as radiation having substantially a single wavelength because of a narrow width of the radiation intensity distribution.

According to the present invention, a plurality of imaging are performed at a plurality of places on an outward route and an inward route by using radiation having different wavelength respectively, and therefore, a plurality of image signals having different radiation wavelength or distance between an object to be inspected and an imaging plane can be efficiently obtained within a short time. Further, phase information about the radiation transmitted through the object is restored on the basis of these image signals to generate image data, and therefore, high quality image data reduced in noise can be obtained.

BRIEF DESCRIPTION OF THE DRAWINGS

FIG. 3 is a flow chart showing a radiation imaging method according to one embodiment of the present invention;

FIG. 5 is a view for explaining correction of detection data in a case of using a point source of radiation;

DESCRIPTION OF THE PREFERRED EMBODIMENTS

Figure 1:
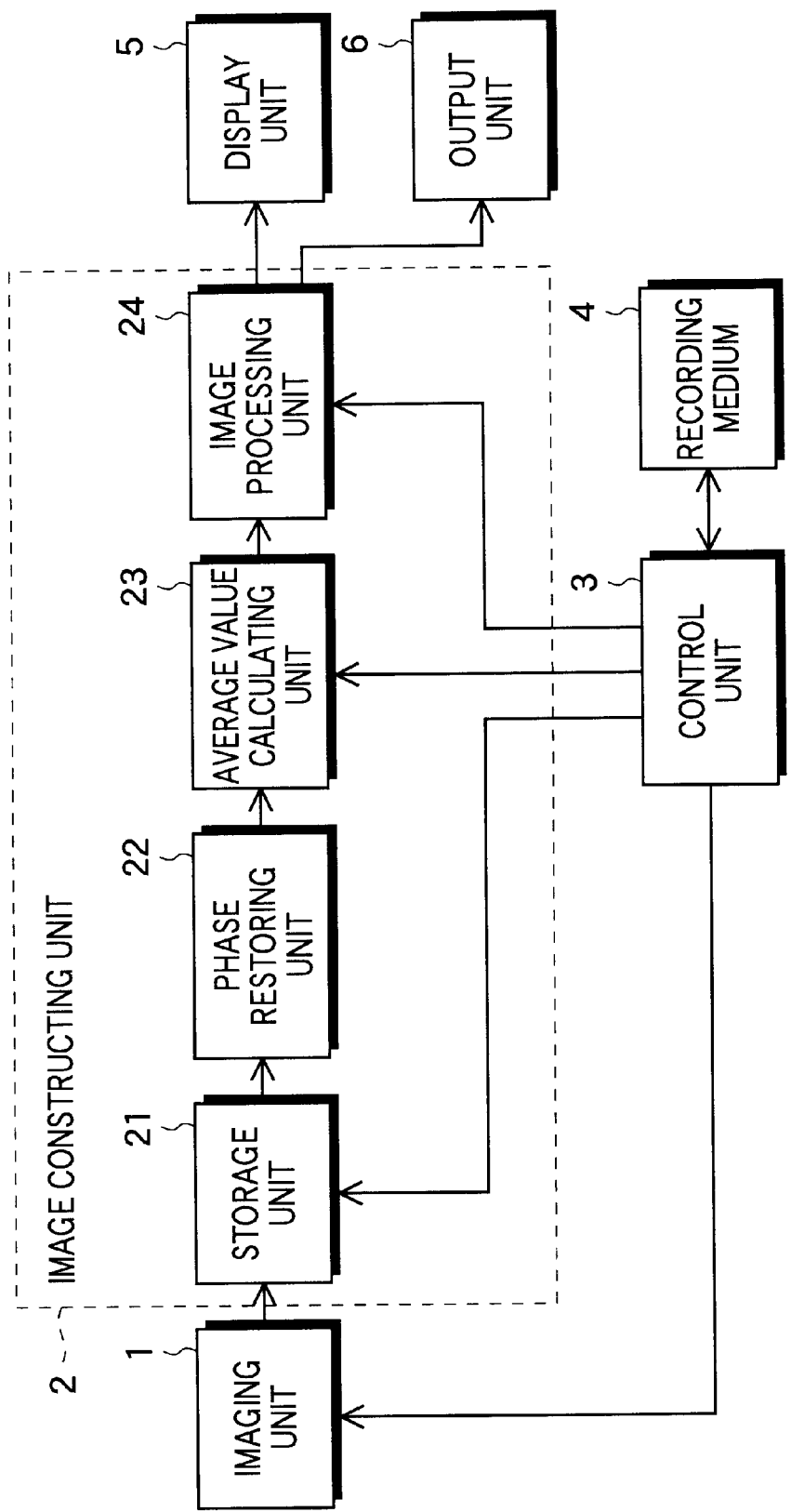
FIG. 1 is a block diagram showing a construction of a radiation imaging apparatus according to one embodiment of the present invention.

Embodiments of the present invention will be described in detail below by referring to the drawings. The same constituent elements will be given with the same reference numerals and the descriptions thereof will be omitted.

FIG. 1 is a block diagram showing a radiation imaging apparatus according to one embodiment of the present invention. The radiation imaging apparatus has an imaging unit 1 for irradiating X-rays on an object to be inspected so as to output image signals representing radiation image information about the object, an image construction unit 2 for restoring phase information on the basis of the image signals so as to generate image data, a control unit 3 for controlling the imaging unit 1 and the image construction unit 2, a recording medium 4 for recording a program and the like for allowing the radiation imaging apparatus to perform an image construction, a display unit 5 for displaying a visible image on the basis of the restored phase information, and an output unit 6 for printing out a visible image on a film or the like.

Figure 2:
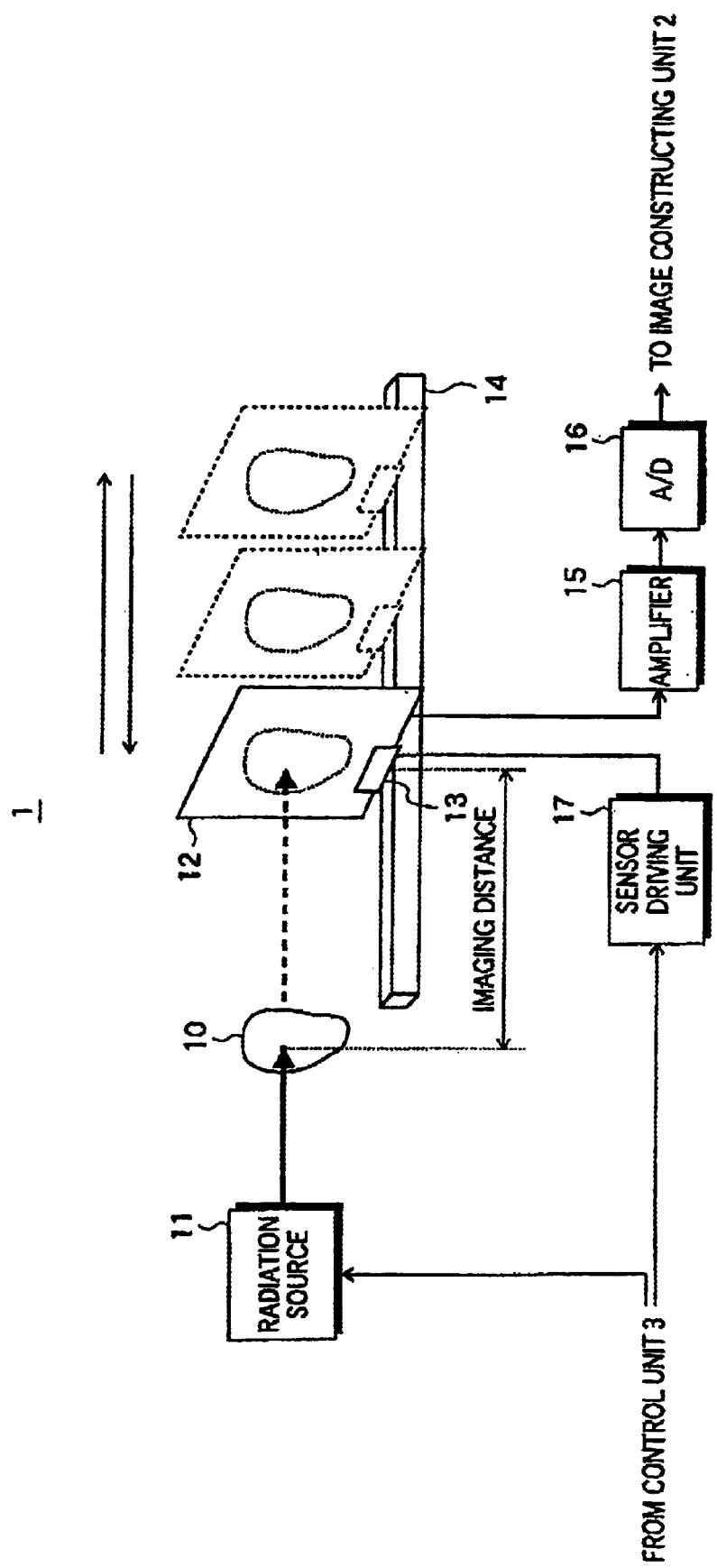
FIG. 2 is a schematic view showing a construction of an imaging unit as shown in FIG. 1.

FIG. 2 is a schematic view showing a construction of the imaging unit 1. The imaging unit 1 has a radiation source 11 and a sensor 12. The radiation source 11 is a variable wavelength radiation source generating a radiation beam. As for the radiation source 11, a radiation source capable of generating a beam having high coherency and high monochromaticity is preferably used. Here, the beam having high monochromaticity means a beam mainly having a single wavelength, however, is not necessarily a beam having a signal wavelength in a strict sense. Accordingly, in this embodiment, a synchrotron radiation source for generating X-rays is used as the radiation source 11. The synchrotron radiation means an electromagnetic wave generated by accelerating an electron or bending a traveling direction of the electron. In such a synchrotron radiation source, wavelength of X-rays generated can be changed by altering acceleration or the like of an electron. The X-rays generated by the radiation source 11 transmit through the object 10 and enter the sensor 12 to produce diffraction fringes.

The sensor 12 is used as a screen for allowing X-rays to enter to produce diffraction fringes and outputs a detection signal representing intensity of an incident diffraction light at each position of the sensor 12. As for the sensor 12, a two dimensional sensor having a plurality of detecting elements, which convert intensity of the incident X-rays into an electric signal to output the electric signal as a detection signal, such as a CAD (charge coupled device) for example, is used.

Further, the imaging unit 1 has an amplifier 15 and an A/D converter 16. The amplifier 15 amplifies the detection signal outputted from the sensor 12. The A/D converter 16 converts the detection signal amplified by the amplifier 15 into a digital signal (referred to as "image signal" or "detection data").

Further, the imaging unit 1 has a holding portion 13 for holding the sensor 12, a rail 14 for supporting the holding portion 13 in a movable state, and a sensor driving unit 17 for driving the holding portion 13. The sensor driving unit 17 changes distance between the object 10 and the sensor 12 by driving the holding portion 13 under the control of the control unit 3, which will be described later. Hereinafter, the distance between the object 10 and the sensor 12 is referred to as an "imaging distance".

Referring again to FIG. 1, the image construction unit 2 includes a storage unit 21, a phase restoring unit 22, an average value calculating unit 23 and an image processing unit 24. The storage unit 21 temporarily stores the detection data outputted from the imaging unit 1. The phase restoring unit 22 restores the phase information at respective imaging distance on the basis of two pieces of detection data which are obtained at equal imaging distance by using two types of X-rays different in wavelength respectively. Further, the average value calculating unit 23 obtains an average value of plural pieces of phase information restored at respective imaging distances. The image processing unit 24 generates image data on the basis of the average value of the restored phase information, and then performs a predetermined image processing such as a gradation processing to the generated image data.

The image construction unit 2 may be constituted of a digital circuit, or of software and a CPU. In the latter case, an image construction program for allowing the respective units 21–24 of the image construction unit 2 to perform a predetermined processing is recorded in a recording medium 4, and the control unit 3 including the CPU processes the detection data on the basis of the image construction program recorded in the recording medium 4. As the recording medium 4, a flexible disk, a hard disk, an MO, an MT, a RAM, a CD-ROM, a DVD-ROMs and so on are applicable.

The control unit 3 controls operation in the respective units 21–24 of the image construction unit 2 and operation of the sensor driving unit 17 or the radiation source 11 included in the imaging unit 1.

The display unit 5 is a display device such as a CRT, for example, and displays a visible image on the basis of the image data representing the phase information restored by the image construction unit 2. The output unit 6 is a laser printer, for example, and prints out a visible image on a film or the like on the basis of the image data.

Next, referring to FIGS. 1–4B, the description will be made on a radiation imaging method according to one embodiment of the present invention. FIG. 3 is a flow chart showing the radiation imaging method according to one embodiment of the present invention. In this embodiment, a diffraction fringe image is imaged while changing wavelength or imaging distance, then a visible image is constructed by using a phase contrast method on the basis of the image signal representing the diffraction fringe image information. Hereinafter, light having wavelength of $\lambda_0$ or $\lambda_1$, which is used for radiation imaging, means highly monochromatic light having the central wavelength of $\lambda_0$ or $\lambda_1$ and it may not be light having a strictly single wavelength of $\lambda_0$ or $\lambda_1$.

Figure 4A:
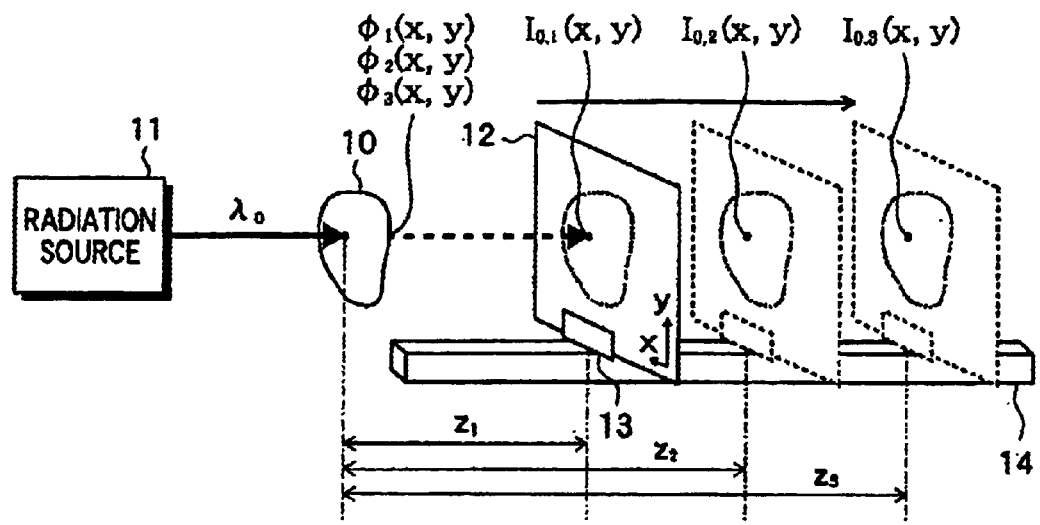
FIGS. 4A and 4B are schematic views for explaining an imaging operation performed in a radiation imaging method according to one embodiment of the present invention.

First, at step S1, the radiation source is set to generate light of wavelength $\lambda_0$ and the X-ray imaging on an outward route is performed while altering a position of the sensor 12 so as to increase distance from the object. More specifically, as shown in FIG. 4A, first, the sensor 12 is disposed at a position of $z=z_1$ and the object 10 is irradiated with the X-rays, thereby performing the X-ray imaging. Next, the sensor 12 is moved to be disposed at a position of $z=z_2$ to perform the X-ray imaging. Further, at a position of $z=z_3$, the X-ray imaging is performed in the same manner.

By the X-ray imaging at step S1, detection data $I_{0,1}(x,y)$, $I_{0,2}(x,y)$, and $I_{0,3}(x,y)$ representing intensity of diffraction light which enters pixel $(x,y)$ on planes of respective imaging distances are sequentially inputted into the image construction unit 2 and stored in the storage unit 21. The detection data represent the diffraction fringe image information on the planes of respective imaging distances.

Figure 4B:
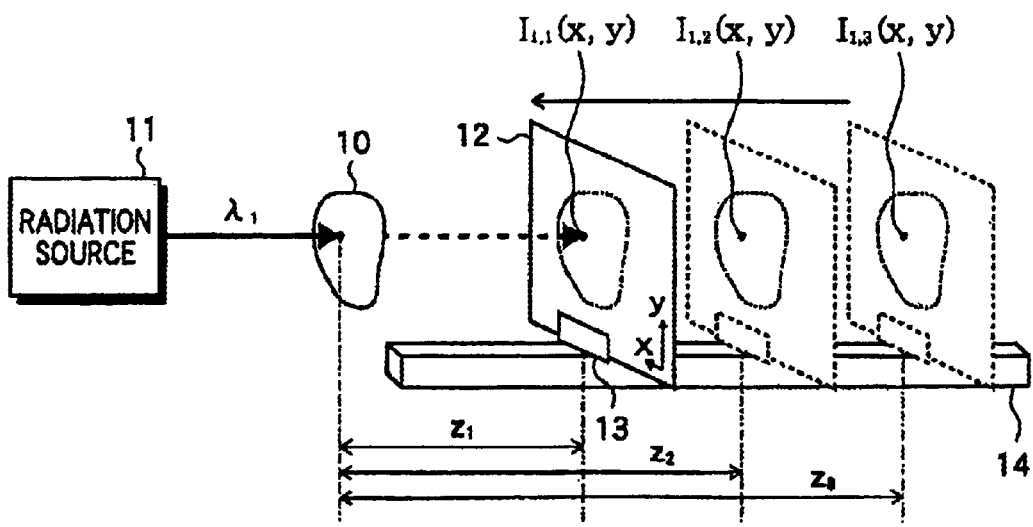

Next, at step S1, as shown in FIG. 4B, the wavelength of the light generated by the radiation source is altered to $\lambda_1$ and the X-ray imaging on an inward route is performed while altering a position of the sensor 12 so as to decrease distance from the object. By this X-ray imaging, detection data $I_{1,3}(x,y)$, $I_{1,2}(x,y)$ and $I_{1,1}(x,y)$ representing the diffraction fringe image information on the plane of the respective imaging distances of $z=z_3$, $Z_2$ and $z_1$ are sequentially stored in the storage unit 21.

Next, at steps S3 and S1, the image construction unit 2 restores the phase $\phi_n(x,y)$ of the X-rays just after having transmitted through the object on the basis of the detection data having equal imaging distance among the detection data $I_{0,1}$–$I_{1,3}$ stored in the storage unit 21. Here, N=1, 2 or 3.

At step S3, the phase restoring unit 22 obtains Laplacian $f_1(x,y)=\nabla^2\phi_1(x,y)$ of phase $\phi_1(x,y)$ on the basis of the detection data $I_{0,1}(x,y)$ and $I_{1,1}(x,y)$ obtained at the imaging distance of $z_1$.

Here, when using the detection data $I_{0,N}(x,y)$ and $I_{1,N}(x,y)$ obtained at the imaging distance of $z_N$ by using two types of X-rays having wavelength of $\lambda_0$ and $\lambda_1$ respectively, Laplace $f_N(x,y)$ of phase is represented as a following expression.

$$f_N(x,y) = -\nabla^2 \phi_N(x,y) = \frac{2\pi}{z_N \Delta\lambda}\{\sigma g_{0,N} - \sigma^{-2} g_{1,N}\} \quad (5)$$

where $$g_{0,N}=ln\{I_{0,N}(x,y)\} \quad (6)$$

$$g_{1,N}=ln\{I_{1,N}(x,y)\} \quad (7)$$

$\sigma=\lambda_1/\lambda_0$, $\Delta\lambda=\lambda_1-\lambda_0$, N=1, 2 or 3.

Accordingly, the detection data $I_{0,1}(x,y)$ and $I_{1,1}(x,y)$ are substituted in the expressions (6) and (7) respectively to obtain $g_{0,1}$ and $g_{1,1}$ and further, $g_{0,1}$ and $g_{1,1}$ are substituted in the expression (5), thereby obtaining Laplace $f_1(x,y)$ of phase. As for derivation of the expression (5), refer to T. E. Gureyev et al. "Quantitative In-Line Phase-Contrast Imaging with Multienergy X Rays", PHYSICAL REVIEW LETTERS Vol. 86, No. 25 (2001), pp. 5827–5830.

At step S1, the phase restoring unit 22 performs an inverse Laplace operation on the Laplacian $f_1(x,y)$ of phase so as to obtain the phase $\phi_1(x,y)$ of the radiation.

Here, the inverse Laplace operation will be described in detail. The Fourier transform of $f_N(x,y)$ is represented as a following expression (8).

$$F[f_N(x,y)]=F[\nabla^2\phi_N(x,y)]=-4\pi^2(u^2+v^2)F[f_N(x,y)] \quad (8)$$

where F[ ] represents Fourier transform and u, v are spatial frequencies corresponding to x, y respectively.

Accordingly, the phase $\phi_N(x,y)$ is represented as a following expression (9).

$$\phi_N(x,y) = F^{-1}\left[-\frac{1}{4\pi^2(u^2+v^2)}F[f_N(x,y)]\right] \quad (9)$$

Here, $F^{-1}[\ ]$ represents inverse Fourier transform.

By utilizing the expression (9), inverse Laplacian operation can be performed. Specifically, $f_N(x,y)$ is Fourier transformed, then multiplied by $\{-4\pi^2(U^2+v^2)\}^{-1}$ and the product is further performed inverse Fourier transform so as to be capable of obtaining the restored phase $\phi_N(x,y)$.

Here, a value of $\{-4\pi^2(u^2+v^2)\}^{-1}$ may be previously calculated within a range, where each of $|u|$ and $|v|$ is not larger than a predetermined value, so that the previously calculated value can be utilized in performing the operation represented by the expression (9). In other words, a predetermined value "const" is set and in the case where $|u|$, $|v|$ $\leq$const, a value of the following expression is used in the expression (9).

$\{-4\pi^2(u^2+v^2)\}^{-1}$=(the previously calculated value) On the other hand, in the case where $|u|$, $|v|$ >const, a value of the following expression is used in the expression (9).

$\{-4\pi^2(u^2+v_2)\}^{-1}=0$

By virtue of this, inverse Laplacian operation can be performed at a high speed.

Such processes at Steps S3 and S4 are performed by using the detection data $I_{0,2}(x,y)$ and $I_{1,2}(x,y)$ obtained at the imaging distance of $z_2$ so as to obtain the phase $\phi_2(x,y)$ of the radiation. Similarly, the processes are performed by using the detection data $I_{0,3}(x,y)$ and $I_{1,3}(x,y)$ obtained at the imaging distance of $z_3$ so as to obtain the phase $\phi_3(x,y)$ of the radiation.

Next, at step S5, the average value calculating unit 23 calculates an average value of the phases from $\phi_1(x,y)-\phi_3(x,y)$ by using a following expression (10).

$$\phi(x, y) = \frac{1}{3} \sum_{N=1,2,3} \phi_N(x, y) \quad (10)$$

By virtue of this, noise level can be reduced to $1/\sqrt{3}$ time and an S/N ratio can be increased to $\sqrt{3}$ times. In general, by using N sets of detection data obtained at N positions, the S/N ratio can be increased to $\sqrt{N}$ times.

Next, at step S6, the image processing unit 24 generates image data on the basis of the restored phase $\phi(x,y)$. Specifically, the image processing unit 24 converts the phases $\phi(x,y)$ in the respective pixels into the image data showing brightness, and then, performs a necessary image processing such as a gradation processing or an interpolation processing to the image data.

Finally, at step S7, the display unit 5 or the output unit 6 displays a visible image on a screen, a film or the like on the basis of the generated image data.

In this embodiment, on the outward route and the inward route, the imaging is performed by three times respectively while altering the imaging distance, however, the imaging may be performed by two times respectively, or by four times or more respectively while altering the imaging distance. When the number of imaging times, namely, that of imaging places is increased, the amount of information to be used for restoring the phase information increases and therefore accuracy of the phase restoration can be more elevated.

Further, in this embodiment, although X-rays are used for imaging an object, not only X-rays but also any other beams may be used as long as the beam transmits through the object to produce a diffraction fringe. As for such a beam, for example, a corpuscular beam including an electron beam can be mentioned.

Furthermore, in this embodiment, although the synchrotron radiation source is used for imaging an object, a radiation source generating a beam that is not the synchrotron radiation may be used. For example, an electron storage type high brightness hard X-ray generator developed by Ritsumeikan University can generate X-rays having high brightness and directivity just like the synchrotron radiation in spite of its tabletop size. X-rays generated by the apparatus have coherency and, even though the X-rays have plural wavelengths, they can be monochromatized by combining with a monochromatizing crystal though they have not a single wavelength. Also, a radiation source developed by the Femtosecond Technology Research Association (FESTA) generates ultrashort pulse high-brightness X-rays on the basis of the principle of backward Compton scattering. The radiation source is compact and portable, and can generate X-rays having not only coherency but also high directivity and monochromaticity.

When a point source of radiation is used as the radiation source, it is preferable to correct the detection data obtained by the X-ray imaging in view of an enlargement ratio before performing a data processing in the image construction unit. FIG. 5 is a view for explaining the correction performed in the image construction unit when using the point source of radiation. In FIG. 5, distance between a virtual origin O of divergent angle of a light beam and the object 10 is represented as $\alpha$. In this case, an enlargement ratio of an image in Nth sensor disposed at $z=z_N$ is $(z_N+\alpha)/\alpha$. Accordingly, the detection data $I_N$ may be subjected to a minification processing of multiplying the data by $\alpha/(z_N+\alpha)$.

Figure 6:
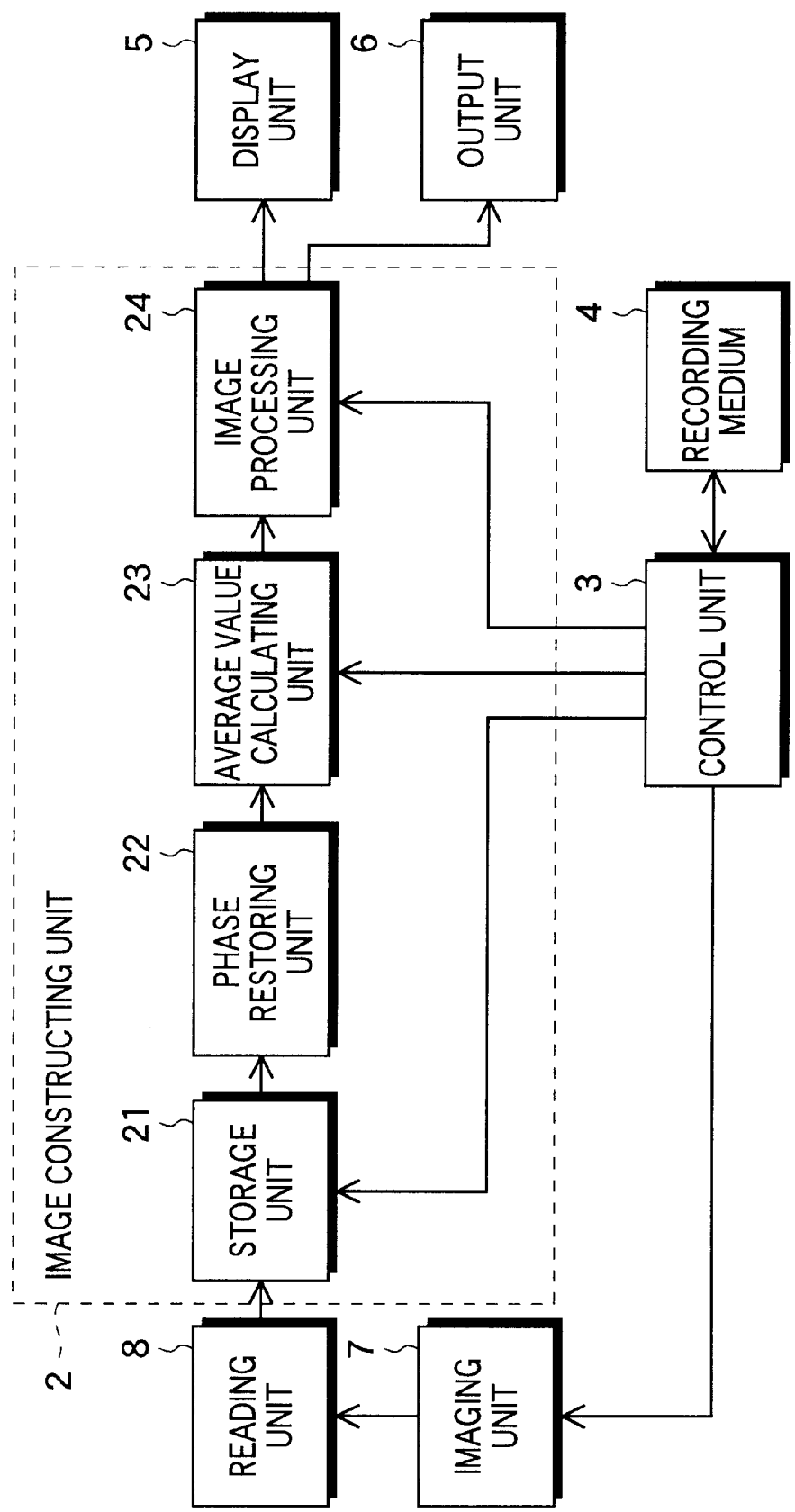
FIG. 6 is a block diagram showing a modified example of a radiation imaging apparatus according to one embodiment of the present invention.

Next, referring to FIG. 6, a modified example of a radiation imaging apparatus according to the one embodiment of the present invention will be explained. The radiation imaging apparatus as shown in FIG. 6 has a reading unit 8 and an imaging unit 7. Other constructions are similar to those of the radiation imaging apparatus as shown in FIG. 1.

In the imaging unit 7, as for a screen to be used for allowing the X-ray to enter to generate a diffraction fringe image, a photostimulable phosphor sheet (recording sheet) is used in place of the sensor 12 in the imaging unit 1 as shown in FIG. 2.

The photostimulable phosphor (storage phosphor) is material that, when irradiated with radiation, stores a part of the radiation energy and that, when an excitation light such as visible light is then applied, emits stimulated fluorescent light corresponding to the stored energy. When a radiation image of an object such as a human body is imaged and recorded on a sheet coated with the photostimulable phosphor and the photostimulable phosphor sheet is scanned with the excitation light such as laser light, stimulated fluorescent light is generated. By photoelectrically reading out the light, the detection data can be obtained. The detection data is appropriately processed and then, outputted to a display such as a CRT or outputted to a laser printer for printing an image on a film, so that the radiation image can be displayed as a visible image.

Figure 7:
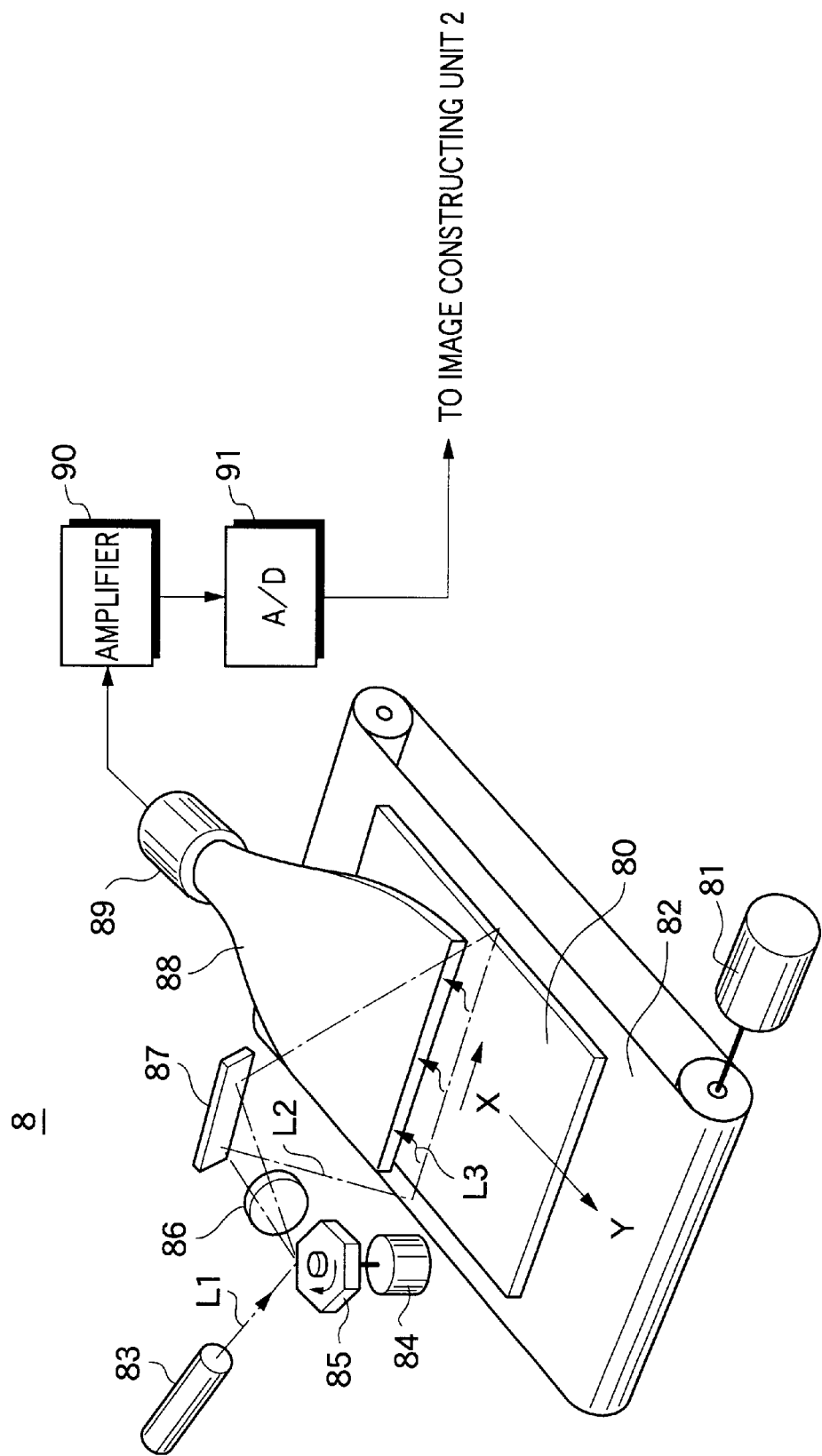
FIG. 7 is a schematic view showing a construction of a reading unit as shown in FIG. 6.
Figure 8:
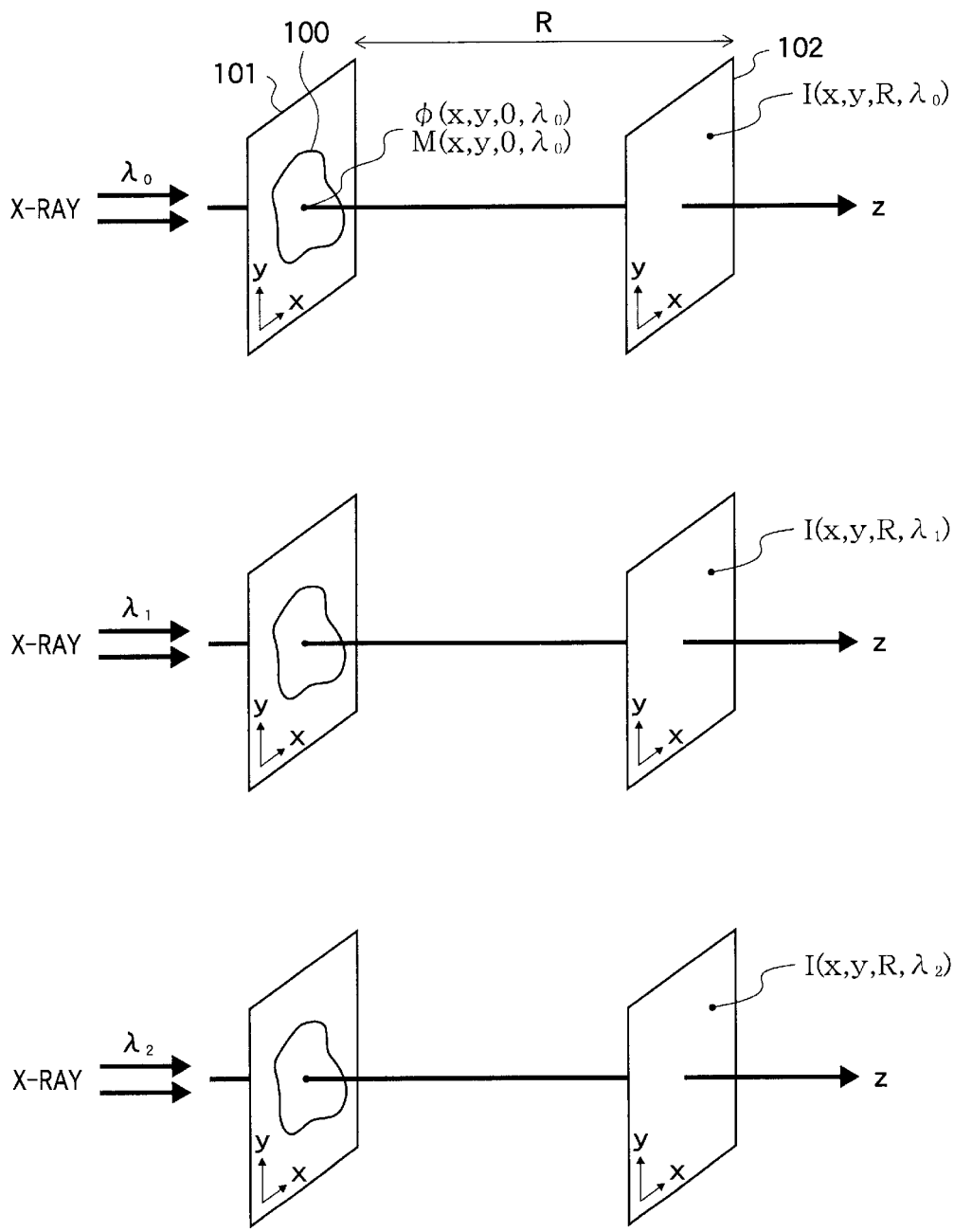
FIG. 8 is a view for explaining the principle of the phase restoration.

The reading unit 8 as shown in FIG. 6 is used for reading out the radiation image recorded in the recording sheet. Referring to FIG. 7, construction and operation of the reading unit 8 will be explained. The recording sheet 80, on which the image information has been recorded, is set in a predetermined position of the reading unit 8. The recording sheet 80 is carried in Y-direction with a sheet carrying unit 82 driven by a motor 81. On the other hand, a beam L1 oscillated from a laser light source 83 is reflected and deflected by a rotating polygon mirror 85 which is driven by a motor 84 to rotate at high speed in a direction indicated by an arrow and passes through a convergent lens 86. Then, the beam L1 changes its optical path by a mirror 87 and scans the recording sheet 80 in X-direction. By the scanning, excitation light L2 is applied to the recording sheet 80 and stimulated fluorescent light L3 having intensity corresponding to the stored and recorded radiation image information is emitted from an applied part. The stimulated fluorescent light L3 is guided by a light guide 88 and photoelectrically detected by a photomultiplier 89. An analogue signal outputted from the photomultiplier 89 is amplified by an amplifier 90 and digitized by an A/D converter 91. A detection signal (data) outputted from the A/D converter 91 is inputted into the image construction unit 2.

The imaging unit 7 performs radiation imaging at respective imaging distances by using a plurality of recording sheets while changing wavelength of radiation on an outward route and an inward route, and the reading unit 8 reads out the image information from the respective recording sheets. As a result, a plurality of detection signals representing diffraction fringe image information having different wavelengths or imaging distances can be obtained. The image construction unit 2 performs phase restoration on the basis of these detection signals to generate the image data. The processing in the image construction unit 2 is similar to that shown in FIG. 3.

As described above, according to the present invention, imaging with using a beam having different wavelength between on an outward route and on an inward route is performed at a plurality of places on each route, as a result, it is possible to obtain efficiently a plurality of image signals representing diffraction fringe image information having different wavelengths or imaging distances within a short period of time. Further, a plurality of phases are restored on the basis of the image signals representing diffraction fringe image information obtained on the planes different in imaging distance and the restored phases are averaged to obtain phase information. Therefore, the phase restoration ensuring high accuracy can be performed. Accordingly, it becomes possible to obtain a high quality visualized image reduced in noise by using the phase contrast method.

What is claimed is:

1. A radiation imaging method comprising the steps of:

(a) sequentially detecting, by using radiation having a first wavelength, intensity of radiation transmitted through an object on a plurality of planes different in distance from the object in a first order of increasing or decreasing the distance from the object so as to obtain a first group of image signals representing radiation image information on said plurality of planes respectively;

(b) sequentially detecting, by using radiation having a second wavelength different from the first wavelength, intensity of radiation transmitted through the object on a plurality of planes different in distance from the object in a second order reverse to the first order so as to obtain a second group of image signals representing radiation image information on said plurality of planes respectively;

(c) restoring phase information of the radiation transmitted through the object on the basis of said first group of image signals and said second group of image signals so as to obtain plural pieces of phase data; and (d) generating image data on the basis of the plural pieces of phase data obtained at step (c).

2. A radiation imaging apparatus comprising:

a variable wavelength radiation source capable of generating radiation having a first wavelength and radiation having a second wavelength different from the first wavelength;

detection means for detecting intensity of radiation transmitted through an object so as to obtain an image signal representing radiation image information;

driving means to be used for altering distance between the object and said detection means;

control means for controlling said variable wavelength radiation source and said driving means in such a manner that said detection means sequentially detects, by using radiation having a first wavelength, intensity on a plurality of planes different in distance from the object in a first order of increasing or decreasing the distance from the object, and then, said detection means sequentially detects, by using radiation having a second wavelength, intensity on a plurality of planes different in distance from the object in a second order reverse to the first order; and image constructing means for restoring phase information of the radiation transmitted through the object on the basis of a plurality of image signals obtained by disposing said detection means at a plurality of positions different in distance from the object so as to obtain plural pieces of phase data, and generating image data on the basis of the plural pieces of phase data.

3. A radiation imaging program allowing a CPU to execute the procedures of:

(a) sequentially detecting, by using radiation having a first wavelength, intensity of radiation transmitted through an object on a plurality of planes different in distance from the object in a first order of increasing or decreasing the distance from the object so as to obtain a first group of image signals representing radiation image information on said plurality of planes respectively;

(b) sequentially detecting, by using radiation having a second wavelength different from the first wavelength, intensity of radiation transmitted through the object on a plurality of planes different in distance from the object in a second order reverse to the first order so as to obtain a second group of image signals representing radiation image information on said plurality of planes respectively;

(c) restoring phase information of the radiation transmitted through the object on the basis of said first group of image signals and said second group of image signals so as to obtain plural pieces of phase data; and (d) generating image data on the basis of the plural pieces of phase data obtained in the procedure (c).

* * * * *